United States Patent [19]

Grossberg et al.

[11] Patent Number: 5,545,550

[45] Date of Patent: Aug. 13, 1996

[54] HUMAN VIRUS ASSOCIATED WITH CHRONIC FATIGUE IMMUNE DEFICIENCY SYNDROME AND ASSAY THEREFORE

[75] Inventors: Sidney E. Grossberg; Vladimir M. Kushnaryov, both of Milwaukee; L. William Cashdollar, Brookfield; Donald R. Carrigan, Wauwatosa; Konstance K. Knox, East Troy, all of Wis.

[73] Assignee: Medical College of Wisconsin, Inc., Milwaukee, Wis.

[21] Appl. No.: 250,314

[22] Filed: May 27, 1994

Related U.S. Application Data

[63] Continuation of Ser. No. 891,452, May 28, 1992, abandoned.

[51] Int. Cl.$^6$ .............................. C12N 5/08; C12N 5/10; C12N 7/00
[52] U.S. Cl. .................... 435/240.2; 435/235.1; 424/207.1; 424/159.1
[58] Field of Search ........................... 435/235.1, 240.2; 424/207.1

[56] References Cited

U.S. PATENT DOCUMENTS

| | | | |
|---|---|---|---|
| 4,647,773 | 3/1987 | Gallo et al. | 435/239 |
| 4,661,445 | 4/1987 | Saxinger et al. | 435/5 |
| 4,708,818 | 11/1987 | Montagnier et al. | 435/5 |
| 4,755,457 | 7/1988 | Robert-Guroff et al. | 435/5 |
| 4,772,547 | 9/1988 | Heimer et al. | 435/5 |
| 4,843,011 | 6/1989 | Sarngadharan et al. | 530/388.35 |
| 5,108,920 | 4/1992 | Ng et al. | 435/239 |

OTHER PUBLICATIONS

J. Palca, *Science*, 254:1726–1728, 1991.
A. Schluderberg, et al., *Annls. of Internal Medicine*, 117:325–331, 1992.
DeFreitas, et al., *Proc. Natl. Acad. Sci.*, 88:2922–2926, 1991.
S. Salahuddin, et al., *Science*, 234:596–601, 1986.
Carrigan et al., *Journal of Infectious Diseases*, 162:844–851, 1990.
Davis, *Microbiology*, 4th ed., Publ.; Lippencott, 267–270, 1990.
Russler, et al., *American Jour. Path.*, 138:1405–1411, 1991.

*Primary Examiner*—Mary E. Mosher
*Assistant Examiner*—Lawrence J. Carroll, II
*Attorney, Agent, or Firm*—Quarles & Brady

[57] ABSTRACT

A method for the detection of the presence or absence of antibodies which bind to antigens of an NMA virus Deficiency is disclosed. This method comprises contacting a solution containing antigens of an NMA virus with a biological sample of a patient and detecting the antibody-antigen complexes. Methods for detection of the presence or absence of antigens or nucleic acid sequences specific to an NMA virus are also disclosed. A substantially purified preparation of an NMA virus and a human cell line chronically infected with an NMA virus are also disclosed.

2 Claims, 5 Drawing Sheets

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 694 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: JHK Virus ( x i ) SEQUENCE DESCRIPTION: SEQ ID NO:1:

-continued

```
CGCGGCCGCG CGTGTGCCAT CACGCCTGGC TAATTTTTAT ATTTTTAGTA GAGACAGGGT    60
TTCGCCATGT TGGCCAGGCT GGTTGCCATG TTGCCAAGGC TGGCCTCAAG CGATCCTCCC   120
TCCCTGGCCT CCCAAAGTGC TGGGATTGCA GGCATGAGCT ACTGCGCCCA ACCTTATTAT   180
GTGTTTTTAA TAGACAAAAA ATAACAAATT AGGAAGAACA AAAATAAATA TGGGCAATAT   240
TCAAATATAT GTAAAGCAAA CAGCAAACTT CTACATTGTT TATGGATCAA AGAAGAAATC   300
AAAGGGAAAT ATAAAAATAT TTTGAATGAA TGAAAACAAA ATCAAAACAT ATCAAAATGT   360
ATAGAATACA GCTGAAGCAG TACTTAGAAG AAAACGTATT GCTTTAAATG CTTATTTTAT   420
AAAGGATTAA ATGTTTAAAA TCAACAATCA AATTACTATC CTAAGAAGTT AGGAAAAGAA   480
GAACAAATCA AACACAAAGT AAGTGTTAAT AGAAACTCAA AGAACAGAAT AAAAATAAAG   540
AGAACCAAAT GTAGACATAC CATAGTCAAA CCACTGGGCA AAAAAAGAG TAAATCTTGA    600
AAGTAGCTAA AGGGAGGGAG AAAATAATTT ACATCCGTGG AAACAAATAG ACAGATGACC   660
TGTCATCAGA AATGACACTT TAAAAAGCGG CCGC                               694
```

HUMAN VIRUS ASSOCIATED WITH CHRONIC FATIGUE IMMUNE DEFICIENCY SYNDROME AND ASSAY THEREFORE

This application is a continuation of application Ser. No. 07/891,452, filed May 28, 1992, abandoned.

FIELD OF THE INVENTION

The present invention relates to assays for viral infections. In particular, the present invention relates to assays for a human virus indicative of CFIDS.

BACKGROIUND OF THE INVENTION

Retrovirus biology

The human virus on which the present invention is based has not been classified as to which virus family it belongs, but it most nearly resembles a retrovirus. Retroviruses are a large family characterized by a single-stranded, positive-sense RNA diploid genome and a reverse transcriptase (Temin and Baltimore, *Adv. Virus. Res.* 17:129–186, 1972) located within the virion nucleocapsid. Retroviruses are similar in virion structure, genome organization, and mode of replication. The order of the major reading frames encoding structural proteins is invariably gag-pol-env. The overall diameter of retroviruses is 60–130 nm, including the envelope with its radially arranged proteins, products of the env gene. Retroviruses are associated with many diseases, such as rapidly evolving and long-latency malignancies, wasting diseases, neurological disorders, and immunodeficiencies (Coffin, J. In: *Fields, Virology,* B. Fields and D. Knipe, ed. Raven Press, N.Y., 2d edition, 2:1437–1500, 1990).

It has been extremely difficult to isolate human retroviruses. Claims of isolation of human retroviruses have been made, but most have subsequently not been substantiated (reviewed in Weiss, et al., *RNA Tumor Viruses; Molecular Biology Of Tumor Viruses,* Cold Spring Harbor, N.Y., vol. 1, 1982, 1291 pp., and vol. 2., 1985, 1233 pp.) To date, the only known exogenous human retroviruses are the cytolytic human immunodeficiency viruses (HIV)-1 and -2 (classified as lentiviruses) and the oncogenic human T-cell lymphotropic (lymphoma/leukemia) viruses (HTLV)-I and -II (classified as oncoviruses). HTLV-I (isolated by Poiesz et al., *Proc. Natl. Acad. Sci.* USA 77:7415–7419, 1980) has been associated with adult T-cell leukemia and tropical spastic paraparesis. HTLV-II has been associated with hairy T-cell leukemia. Another group of isolated human retroviruses, the foamy or spumaviruses, are not known to be pathogenic (Coffin, 1990, supra).

Another unique feature of retroviruses is their presence as inherited elements in the germline of many vertebrates where they behave as reasonably stable Mendelian genes. The so-called endogenous viruses may comprise as much as 5–10% of a mammalian genome, consisting of elements introduced by mechanisms involving reverse-transcription, similar to retrotransposons of lower evolutionary orders. It is likely that there are no human cell lines that are free of endogenous retroviral sequences (Steele et al., *Science,* 225:943–947, 1984; Shih et al., *Virology,* 63:64–75, 1989).

CFIDS

Chronic fatigue immune deficiency syndrome ("CFIDS," also called neuromyasthenia (NMA) or myalgic encephalomyelitis, among others) is a poorly defined illness that is characterized by debilitating fatigue and associated with some immunologic, hematologic, and neuromuscular abnormalities (Straus, S. E., *J. Infect. Dis.,* 157:405–412, 1988; Holmes et al., *Ann Intern. Med.,* 108:387–389, 1988; Lloyd et al., Lancet, i:1286–1287, 1988; Swartz, M. N., *N. Engl. J. Med.,* 319:1726–1728, 1988; Schooley, R. T. In: *Current Clinical Topics In Infectious Diseases,* Remington, J. and Swartz, M. N. (eds.) McGraw-Hill, New York, pp. 126–1146, 1988; Straus et al., *N. Engl. J. Med.,* 319:1692–1698, 1988). The symptoms include cognitive impairment, especially of memory and concentration, depression, general fatigue, sleep disorders, headache, arthralgia, sore throat, muscle fatigue on repetitive movement, and muscle pain or tenderness. The signs can also include low-grade fever, lymphadenopathy, and localized muscle group weakness. Some patients do poorly on certain psychometric tests. A variety of immunologic abnormalities have been associated with CFIDS, including cutaneous anergy to a variety of common antigens (implying a defect in cell-mediated immunity), low natural killer cells, poor mitogenic response of lymphocytes, reduction in various lymphocytic markers, or atypical lymphocytes, none of which is diagnostic. Other than evaluation of a patient's symptoms, there is no assay for CFIDS.

There are estimated to be at least 100,000 CFIDS patients in the U.S. CFIDS usually occurs sporadically in children and adults or in a few instances as localized outbreaks (e.g., Lake Tahoe, Nev. in adults; Lyndonville, N.Y., in children in 1985). Although morbidity may be high, sometimes for many months, and relapses occur, there are no documented fatalities. There is no clear-cut associated histopathology to help document the nature of the illness.

Various viruses thought to be implicated as possibly contributing to CFIDS include Epstein-Barr Virus (EBV), human herpesvirus-6 (HHV-6), and enteroviruses. However, no virus has convincingly been proven to cause CFIDS. There has been a report of possible retrovirus involvement: DeFreitas, et al., (*Proc. Natl. Acad. Sci.,* USA, 88:2922–2926, 1991) have recently reported a polymerase chain reaction-amplified DNA product in the blood of CFIDS patients. This DNA product hybridizes with HTLV-II gag sequences.

What is needed is an assay for CFIDS involving an associated human virus.

SUMMARY OF THE INVENTION

The present invention is a method for the detection of the presence or absence of antibodies which bind to antigens of an NMA virus, which is indicative of the neuromyasthenia that is characteristic of CFIDS. This method comprises contacting a solution containing antigens of an NMA virus with the biological sample of a patient for a time and under conditions sufficient for the antigens in the solution and antibodies in the biological sample to form antibody-antigen complexes and then detecting the antibody-antigen complexes. By "biological sample" we mean to include any biological material, such as blood, tissue, or cells, which might be infected with the NMA virus or harbor antibodies, antigens, protein, or nucleic acid fragments specific to an NMA virus.

The present invention is also a method for the detection of the presence or absence of antigens specific for an NMA virus. This method comprises raising antibodies against an NMA virus antigens and contacting said antibodies with the biological sample of a patient for a time and under conditions sufficient for the antibodies and antigens in the biological sample to form antigen-antibody complexes and then detecting the antibody-antigen complexes.

The present invention is also a method for the detection of the presence or absence of nucleic acid sequences substantially similar to those encoded by an NMA virus. This method comprises contacting a nucleic acid probe which has been obtained from a cloned fragment of an NMA virus with a nucleic acid sample from a patient for a time and under sufficient conditions for the nucleic acid probe and sample to hybridize and then detecting the nucleic acid hybrids.

The present invention is also a method for the production of NMA virus comprising cultivating a cell line infected with an NMA virus and isolating an NMA virus from the cells.

In a particularly advantageous embodiment of the invention, the NMA virus is substantially similar to the JHK virus. By "substantially similar," we mean that the virus is morphologically and biochemically similar to JHK virus and is immunologically cross-reactive.

The present invention is also a purified preparation of JHK virus and a human cell line chronically infected with JHK virus. In a preferable form of the invention, the human cell line is JHK-3 cells (ATCC Accession No. CRL 10991).

An object of the present invention is to provide a means for diagnosing an immunoneuromuscular disease in patients.

Another object of the present invention is to provide a means for diagnosing CFIDS in patients.

It is an advantage of the present invention that biochemical and immunological assays for CFIDS are provided that will complement the present method of diagnosing CFIDS, which is an analysis of a patient's symptoms.

Other objects, advantages and features of the present invention will become apparent from the following specification when taken in conjunction with the accompanying claims.

DESCRIPTION OF THE PREFERRED EMBODIMENT

Figure 1D:
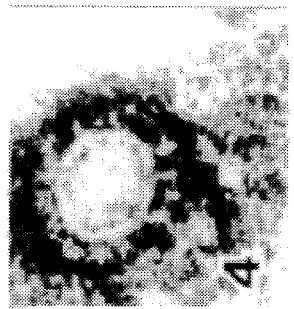
FIG. 1A, FIG. 1B, FIG. 1C and FIG. 1D are electron micrographs of JHK virions at X 200,000 magnification.
Figure 1C:
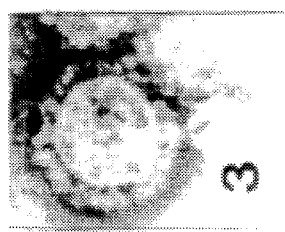
Figure 1B:
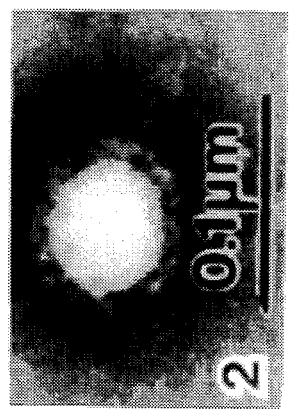
Figure 1A:
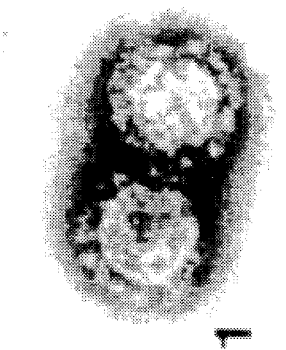

The present invention relates to the detection of the presence of an NMA virus that is associated with CFIDS. This detection has utility in both diagnosis and treatment of CFIDS. The detection may be by means of detecting antigens specific to the virus, antibodies specific to the virus, nucleic acid sequences specific to the virus, proteins specific to the virus, or the virus itself.

In brief, we have identified morphologically identical viral particles budding from the lymphocytes of three different CFIDS patients. We have named this virus the "NMA virus." We have extensively studied one isolate, JHK virus.

1. Preliminary characterization of JHK virus and JHK 3 cells. The JHK virus was initially isolated from Patient 1. Patient 1 is a 40-year old woman who had experienced a relatively acute onset of severe fatigue, marked easy fatigability, difficulties in mentation, neuromuscular symptoms, immunologic anergy, and no haematologic evidence of leukemia or lymphoma. These symptoms lasted about three years and led to a diagnosis of CFIDS.

Patient 1 gives a typical history of CFIDS. She had periods of several months of profound fatigue, somnolence requiring prolonged bedrest, impaired cognition, muscle weakness, paresthesias, weight loss, lymphadenopathy, and fever. She experienced occasional, neuromuscular episodes manifest primarily as localized weakness, and occasional arthralgias, as well as rare, drenching night sweats. The subsequent use of a battery of seven skin test antigens revealed immunologic anergy. No leukemic cells have been detected in stained peripheral blood smears, although a few atypical lymphocytes were observed. Serum from Patient 1 is negative for antibodies to HIV and HTLV-I, with a low titer of 1:80 to Epstein-Barr virus capsid antigen and a borderline, detectable level (1:10) of antibody reactive with EBV nuclear antigen (EBNA).

Samples of Patient 1's blood were taken in January, April, and September of 1989, and February 1990. We examined the Ficoll-Hypaque-purified peripheral blood mononuclear cells (PMCs) from her blood by electron microscopy. All these samples have shown mononuclear cells, many of which have distorted nuclei, with 80–85 nm, enveloped viral particles budding from the plasma membranes of B-lymphocytes.

Utilizing a technique successfully used for isolating HIV, HTLV, and HHV-6 from peripheral blood leukocytes which is indicative of the neuromyasthenia that is characteristic of CFIDS, the patient's PMCs (from the September 1989 bleeding) were cultured in the presence of normal donor lymphocytes that had been stimulated 72 hours previously with phytohemagglutinin (PHA) in medium containing fetal bovine serum and interleukin-2 (IL-2). We call the normal donor lymphocytes "ND cells." After about 2 months of cultivation, the cultured cells began to degenerate and cell-free, supernatant medium from this culture was added to PHA-stimulated PMCs from a healthy donor whose lymphocytes did not show viral particles.

Subsequently, the cell population began to increase and continued to grow in the absence of IL-2. We named this cell line "JHK-3." Flow cytometry revealed in early passages of the cell line an antigen-marker distribution resembling that of a pre-B lymphocyte or monomyelocytic stem cell. (The antigen markers were B4, CD10, and $I_2$->90%; My7, My9->70%; T1, positive in chronic lymphocytic leukemia, ->87%.) Later passage cells showed somewhat more differentiated B-cell markers (B4, B1, CD10, and $I_2$, as well as IgM and IgD without Tac antigen). Thus, the JHK-3 cells were not of T-lymphocyte origin. (T-lymphocytes are the major target for the HIV and HTLV retroviruses.)

In addition, JHK-3 cells are (i) positive for EBV nuclear antigen by immunofluorescence analysis and for EBV DNA by PCR analysis; (ii) negative for HHV-6 antigen by immunofluorescence analysis and HHV-6 DNA by PCR analysis; (iii) negative for HIVp24 antigen by enzyme immunoassay and for HIV proviral DNA by PCR analysis; and (iv) negative for HTLV-I and HTLV-II DNA by PCR analysis. By electron microscopy, most JHK-3 cells show irregularly shaped nuclei. Cytogenetic examination of 50 metaphases of chromosomes of low-passage JHK-3 cells showed that they have markedly abnormal karyotypy, with a chromosomal distribution of 23 to 95 (normal-46). Later passages show marked aneuploidy.

JHK-3 cell cultures are propagated in RPMI-1640 medium containing 15% fetal bovine serum and no added growth factors. Stocks of early and subsequent passages of these cells have been preserved frozen in dimethyl sulfoxide-containing medium at −80° C. and demonstrated to be viable and productive of virus on thawing and cultivation. We have deposited a sample of JHK-3 cells with the American Type Culture Collection (ATCC), Rockville, Md. on March 18, 1992 as CRL 10991.

Electron microscopy of thin sections of JHK-3 cells has demonstrated two different viral particles: (1) a preponderant, 80–85 nm, enveloped particle (called JHK virion) which appear to be identical to the budding particles seen in the fresh, uncultured PMCs of Patient 1; and (2) a less frequent 196-nm enveloped particle. The 196-nm particles are found within cytoplasmic vesicles or closely associated with the plasma membrane of the JHK-3 cells but are not seen in the PMCs of either the patient or the normal donor ND. This 196-nm virus may be Epstein-Barr (EBV) virus on the basis of labeling with anti-EBV gp 350/220 monoclonal antibody, but it has not yet been conclusively identified.

Pellets obtained by ultracentrifugation of various cell-free JHK-3 culture supernatants from passages 2 to 19, contain the 80-nm, enveloped virus particles.

We have found a virus similar to JHK virus in two other CFIDS cases, Patient 2 and Patient 3. Patient 2 is a 44-year-old white male with a 2-year history of CFIDS-like symptoms. Patient 2 experienced a 6-month period of extreme fatigue, sleeping 16–18 hours/day, postexertional malaise, muscle weakness, lymphadenopathy, splenomegaly, arthralgias, morning stiffness, impaired cognition, dizziness, depression and anxiety. Patient 3 is a 45-year old female, who experienced about five years of fatigue, myalgias, chronic pharyngitis, low-grade fever, depression and impaired cognition.

We call the viruses that have been identified from these CFIDS patients "NMA viruses" (for the neuromyasthenia that characterizes CFIDS). The JHK virus is an example of one isolate of an NMA virus. The viruses identified in Patients 2 and 3 are other examples.

2. Viral Concentration and Purification.

We have partially purified JHK virus from JHK-3 cells by a sucrose gradient. We envision that other NMA viruses can be substantially purified by similar methods. By "substantially purified" preparation, we mean a viral preparation that is sufficiently pure to be useful in formulating diagnostic assays. For example, the JHK virion preparation described below was used to raise antibodies, to visualize JHK virions by EM, and in a Western blot. Our standard purification is as follows:

Supernatant fluid from dexamethasone-induced JHK-3 cell cultures containing JHK virus metabolically labeled with $^3$H-uridine was filtered through 0.45 nm and 0.22 nm membranes and concentrated by ultracentrifugation at 100,000× g. The viral pellet was resuspended in about 200 μl NTE buffer (Tris-EDTA-NaCl), placed on a preformed, nuclease-free sucrose (10–60%) gradient, and centrifuged 1 hour at 100,000 ×g. About 20 fractions were then collected, and the resultant peak fractions, in which trichloracetic acid precipitable RNA was detected by quantitative scintillation radiometry, were pooled. The pooled fractions were diluted in about 17 ml of NTE buffer (Tris-EDTA-NaCl), and centrifuged again at 100,000×g. The viral pellet was resuspended, as above, and placed on another sucrose gradient, as above. The resultant peak fractions were pooled, diluted as before, and re-centrifuged. This resuspended, doubly-banded virus preparation upon examination by electron microscopy showed no contaminating EBV-like virions and only a small amount of cellular membranes.

Large-scale viral concentration and purification may be accomplished by double banding by sucrose density gradient ultracentrifugation (Poiesz, et al., *Proc. Natl. Acad. Sci.*, 77:7415–7419, 1980) or Percoll gradients (Pertoft and Laurent, In: T. G. Pretlow II and T. P. Pretlow (ed), *Cell Separation: Methods And Selected Applications*, vol. 1. Academic Press, Inc., New York, (Percoil), p. 115–152, 1982; Miyazawa et al., *J. Exp. Med.*, 166:890–908, 1987) to avoid the dilution of virus and interference with EM preparation that we have experienced with sucrose purification. We routinely employ serial filtration of culture supernatants through 0.45 and 0.22 μm filters to remove a putative endogenous inhibitor of reverse transcriptase and the large amounts of cell fragments and vesicles that JHK-3 cells shed.

3. Electron Microscopy of JHK virions.

By EM and the use of negative staining with salts of heavy metals, we have partially physically characterized JHK virions. JHK viral particles were partially purified by sedimentation at 100,000–200,000 ×g for 1 hour (or 30,000×g for 4 hours, at which virion morphology is better preserved) from JHK-3 cell supernatant fluids. The concentrated and partially purified JHK virus was fixed in 0.5% glutaraldehyde and prepared by standard techniques (Nermut et al., In: *Animal Virus Structure*, M. Nermut and A. Steven (eds), pp. 21–33 and pp. 35–39, Elsevier, Amsterdam, 1987) using 2% sodium phosphotungstate, pH 6.8 or uranyl salts. FIG. 1A, FIG. 1B, FIG. 1C and FIG. 1D are electron micrographs of four different views of JHK virions at ×200,000 magnification.

These particles were found to have a diameter of 79.8 nm±0.9 SEM (n=40). Negative staining of the virus in these pellets showed a centrally located nucleocapsid core and knobbed, protein spikes (peplomers) in the envelope, which are characteristic of most retroviral types. The knobbed protein spikes that traverse the envelope measure 12 nm. The diameter of the nucleocapsid, not clearly definable in all particles, is 34.7 nm± 1.1 (n=16).

Thus, the size and shape of the JHK virion distinguishes it from the size of other enveloped RNA viruses (e.g., togaviruses are 60–65 nm, flaviviruses are 45 nm, human or mammalian retroviruses are 100–120 nm and the arenaviridae are 110–130 nm). Further, the shape of JHK virions appears to be distinct from non-retroviruses of similar size, such as the bunyaviridae, 80–110 nm.

A distinctive characteristic of the JHK virions is the length of the peplomers, being longer (12 nm) than those of the togaviruses or most other retroviruses (about 5–6 nm) and shorter than those of coronaviruses (20–22 nm), whose overall diameter measures 80–110 nm. Mouse mammary tumor virus, a retrovirus, has peplomers of 11–12 nm.

4. JHK virions in ultrathin sections of JHK-3 cells and patients' lymphocytes. In electron micrographs, we have found JHK virus budding from the plasma membrane, within intracytoplasmic vesicles, and as free particles near the cell membrane. The diameter of virus particles in thin sections of cells (calculated as recommended by Williams, *Quantitative Methods in Biology*, North Holland Publ., New York, pp. 49–62, 1977) is 85.3 nm±2.8 (n=54), which is in the same size range as the virus observed in the lymphocytes of patients 1, 2, and 3. For comparison, we measured the murine leukemia virus (MuLV) strain LP-BM5 in SC-1 cells to be 119 nm± 2.1 (n=18) and of human T lymphotrophic virus I (HTLV-I) in the high-producer MT-2 cell line (provided by Dr. Bernard Poiesz) to be 111.8 nm± 2.8 (n=50). Both MuLV and HTLV-I-infected cells were prepared by procedures identical to those indicated above. Our measurements of MuLV and HTLV are similar to those reported by others. The size difference in the JHK virus in both the lymphocytes of Patient 1 and JHK cells compared with HTLV-I or MuLV (LPBM 5) viruses in thin sections is statistically highly significant.

Figure 2A:
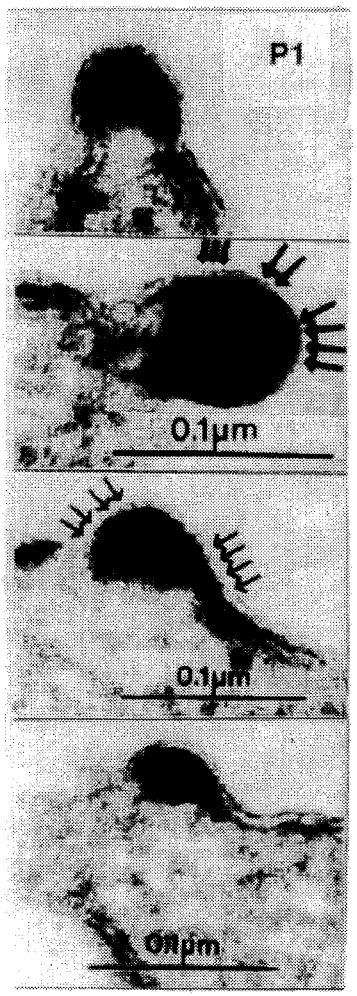
FIGS. 2A, FIG. 2B, FIG. 2C, and FIG. 2D are a college of electron micrographs of virus budding from the lymphocytes of Patient 1 (FIG. 2A), Patent 2 (FIG. 2B), Patient 3 (FIG. 2C) and JHK cells (FIG. 2D).
Figure 2B:
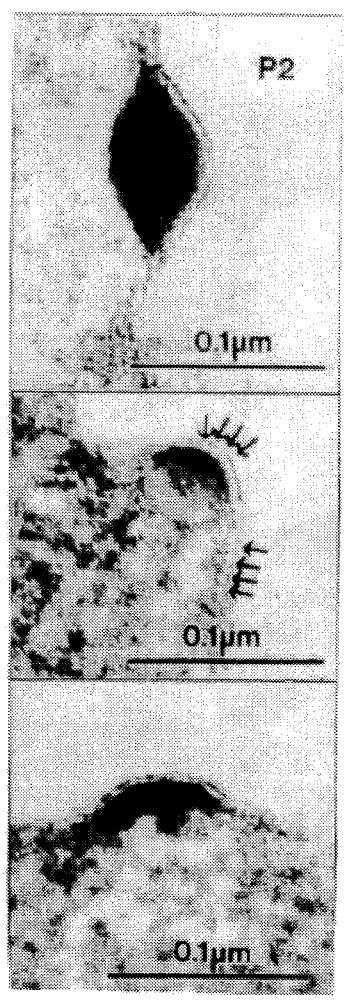
Figure 2C:
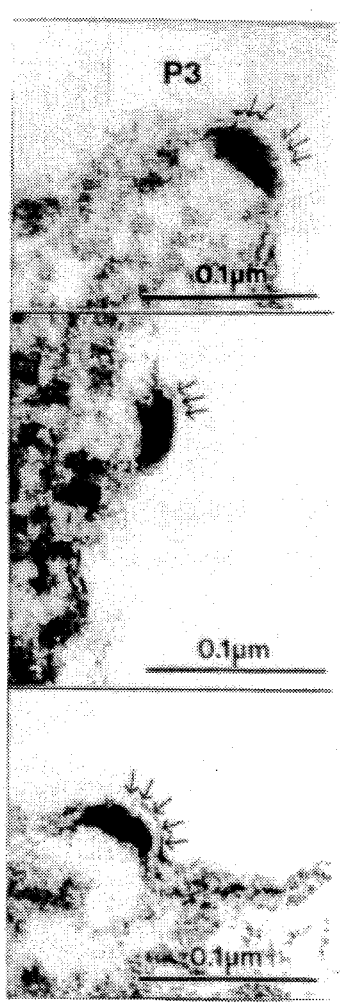
Figure 2D:
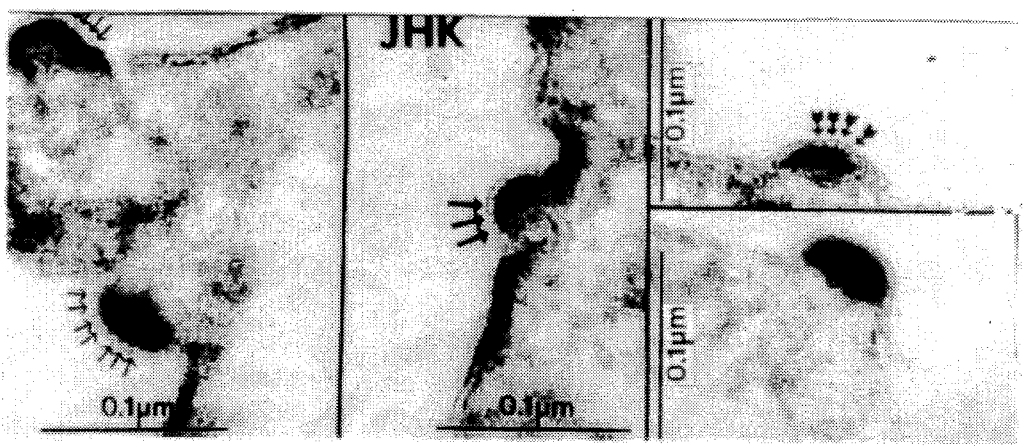

Electron micrographs demonstrated that the budding of the LP-BM5 and HTLV-I retroviruses is different from JHK virion budding. Under the membrane of JHK virus-producing cells, electron-dense material staining intensively with uranyl acetate appears to fill the budding projection often in a lenticular form, whereas most retroviral budding is seen as a thin, crescentic line of electron-dense material separated from the membrane by an electron-lucent zone. The morphological characteristics of the particles in JHK-3 cells and in the lymphocytes of Patient 1 are essentially the same. No EBV-like virus particles were seen in any PMCs of Patient 1 or in those of CFIDS Patients 2 and 3, whose lymphocytes also showed morphologically identical 85-nm budding virus particles. FIG. 2A, FIG. 2B, FIG. 2C and FIG. 2D are electron micrographs taken at original magnification of ×60,000 of virus observed in the PMCs from Patient 1 (FIG. 2A), Patient 2 (FIG. 2B), Patient 3 (FIG. 2C) compared with those in JHK cells (FIG. 2D). The arrows indicate the characteristic scalloping of the membrane overlying the budding particles. The virions are similar in size and appearance in the lymphocytes of Patients 1, 2 and 3 and in JHK-3 cells.

Figure 3:
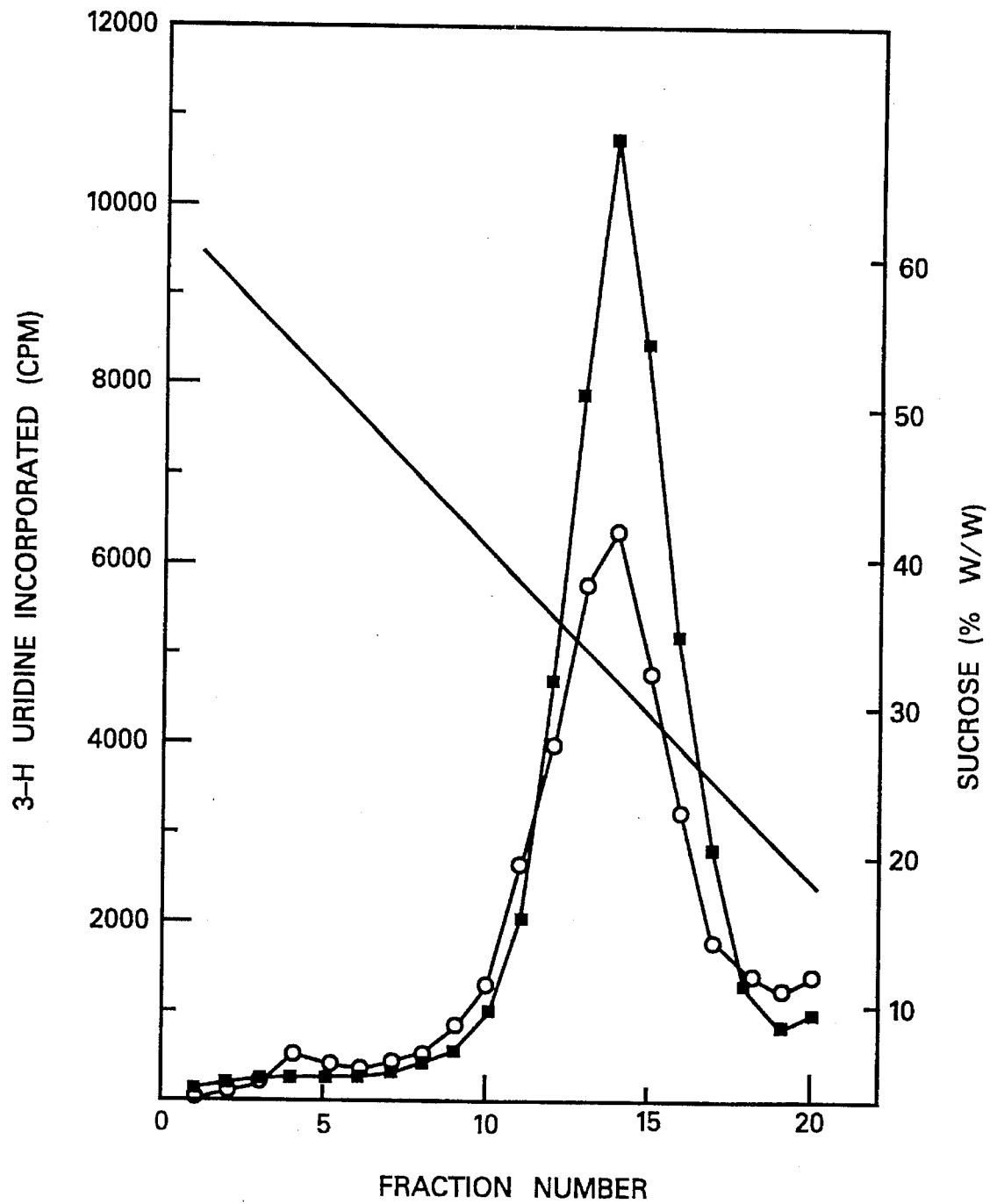
FIG. 3 is a graphical analysis of a sucrose gradient purification of JHK virus.

5. RNA Composition of JHK virus. To determine the nature of the nucleic acid in the constitutively released 80-nm viral particles, JHK-3 cell cultures were pretreated for 2 or 3 days with 1 µM dexamethasone and then metabolically labelled for 24–40 hours with 10–20 µCi/ml $^3$H-uridine or $^3$H-thymidine. Ultracentrifugation of cell-free, supernatant fluids produced virus pellets, which were resuspended, placed on 10–60% nuclease-free, sucrose gradients, and centrifuged at 200,000 ×g for one hour. The fractions from the $^3$H-uridine-treated cultures showed a peak of trichloracetic-acid (TCA)-precipitable radioactivity with a density 1.13–1.17 g/cm$^3$, in the range reported for retroviruses. FIG. 3 is a graph of sucrose gradient fraction number versus $^3$H-uridine incorporation. The more prominent peak (indicated by squares) represents counts of $^3$H radioactivity in viral particles sedimented from culture fluid after centrifugation at 200,000×g, and the less prominent peak represents counts from culture fluid after centrifugation at 30,000×g for 4 hours prior to being placed on the gradient. The morphology of virions was better preserved in pellets sedimented at the lower centrifugal force. The diagonal line represents the sucrose gradient measured by optical refraction. Labeling with $^3$H-thymidine provided no peak of TCA-precipitable labeled DNA. Thus, we determined that the virions contain only RNA. Further, ribonuclease treatment of ultrathin sections of JHK-3 cells produces electron-lucent cores (ghosts) of the 80-nm particles, indicating an RNA composition, with no alteration of the nucleoids of the 196-nm particles.

6. Attempts to enhance JHK virus induction and JHK-3 cell growth. As reported for MuLV retroviruses (Teich, et al., *Virology*, 51:163–173, 1973), 1 µM dexamethasone added to JHK-3 cells for 4–5 days enhances JHK virus production, as indicated by an increased number of particles by EM, reverse transcriptase activity, and higher peaks of 3Huridine incorporation in sucrose density gradients. Dexamethasone at 2 µM and 3 µM was cytotoxic. Although JHK-3 cells in spinner culture died, the cells grew well in large volumes in roller bottles. Addition of growth factors, such as granulocyte/macrophage colony stimulating factor (GM-CSF), macrophage colony stimulating factor (M-CSF), and platelet-derived growth factor, in varied doses, did not enhance cell growth.

Figure 4:
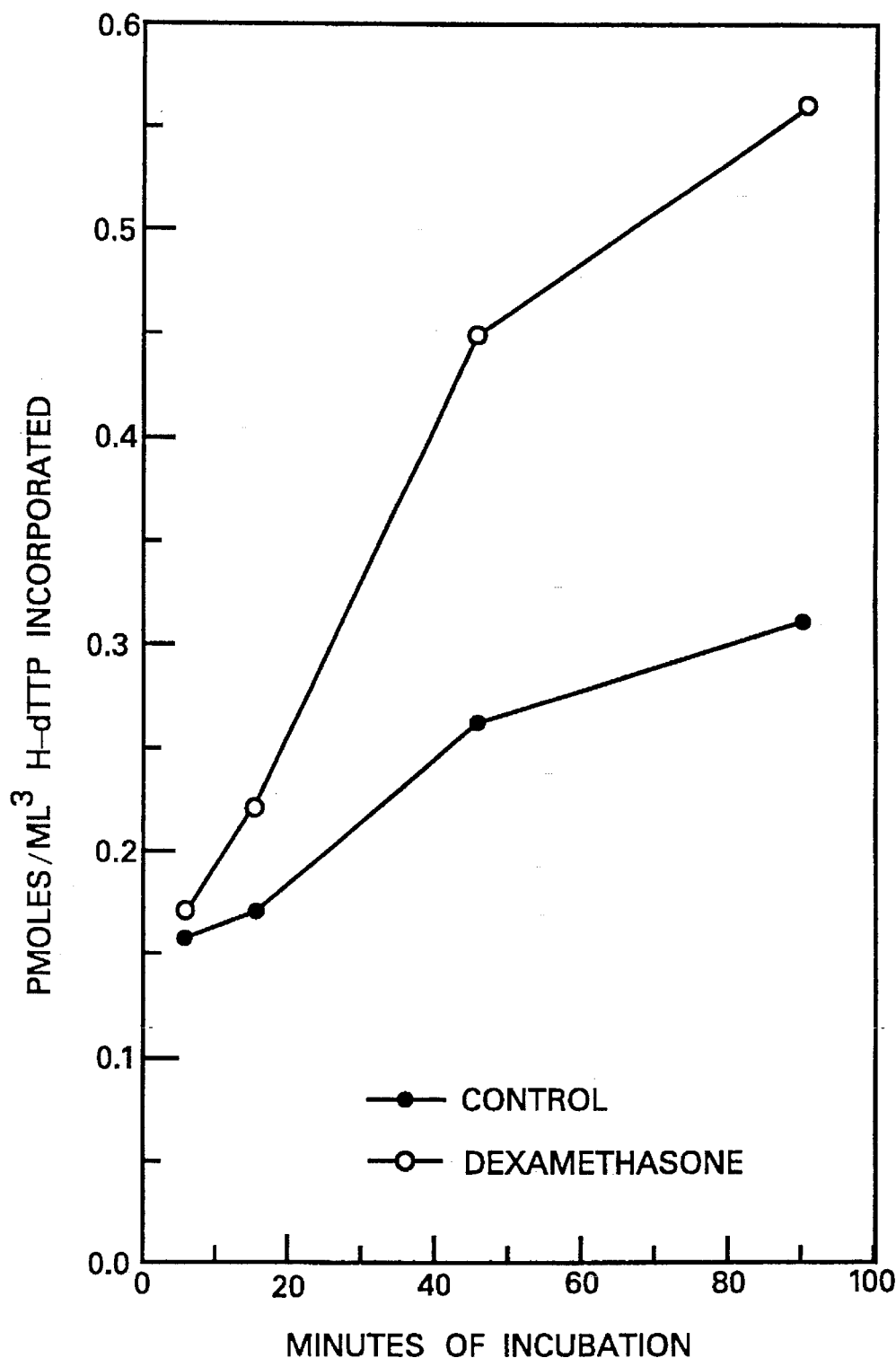
FIG. 4 is a graphical analysis of a reverse transcriptase assay.

7. Reverse transcriptase activity. The presence of the enzyme reverse transcriptase (RT) is characteristic of a retrovirus. RT activity was demonstrated in JHK viral pellets. Our assay solution included poly(rA).oligo(dT)$l_{12-18}$ as the template-primer, $^3$H-dTTP, and 5–10 mM Mg$^{++}$ at 37° C. The RT reaction mixture contains, in 50 µl: 15 µCi $^3$H-dTTP, 50 mM Tris-HCl pH 7.8, 83 mM KCl, 5 mM MgCl$_2$, 50 µM ZnSO$_4$, 0.5 mM EGTA, 0.05% NP-40, 3.0% glycerol, 5 µg/ml poly(rA).oligo(dT), 20 mM DTT, and 0.1 mM of dATP, dCTP, and dGTP. The enzyme was labile in the absence of dithiothreitol (DTT), detergent, or glycerol, as are other RTs. Treatment of JHK-3 cells with 1.0 µM dexamethasone increased the height of the $^3$H-uridine incorporation peak, the virion number as assayed by EM, and reverse transcriptase activity. (Cellular DNA polymerases decrease after corticosteroid treatment, Purohit et al., *J. Steroid. Blochem.*, 34:443–446, 1989; Tesoriere et al., *J. Neurochem.*, 52:1487–1494, 1989.) FIG. 4 is a graph recording the results of an RT assay. Detection of this reverse transcriptase activity has been variable.

8. Transfection. Different amounts of JHK-3 cell DNA (1 µg, 3 µg and 10 µg), presumably containing JHK provirus, were introduced by cationic liposome-mediated transfection (Felgner, et al., *Proc. Natl. Acad. Sci.*, USA, 84:7413–7417, 1987) into three B-lymphoblastoid cell lines (from Dr. William Sugden, University of Wisconsin, Madison.) One line, HH514, was EBV-positive and two lines, BJAB and Wilson, were EBV-negative. After transfection, the BJAB cells did not grow, but the Wilson and HH514 cells propagated well. After 6 weeks supernatant fluid was centrifuged at 200,000×g to obtain a pellet, and the pellet and cells examined by electron microscopy. The HH514 cells transfected with 10 µg of JHK cell DNA were positive for 80-nm virions and incorporated $^3$H-uridine such that the 200,000×g viral pellet gave a characteristic peak of TCA-precipitable radioactivity in a sucrose density gradient. Thus, transfection with JHK-3 cell DNA was successful, providing additional evidence that JHK virus is a retrovirus.

9. Reverse transcription of JHK viral RNA and cDNA cloning. To obtain JHK viral cDNA clones, we synthesized cDNA with purified MuLV reverse transcriptase, using JHK viral RNA as a template. The JHK viral RNA was extracted from JHK virus that was purified by sucrose gradients. The RT reaction was primed with oligo-dT and performed as described by Pharmacia PL, the supplier of the reverse transcriptase kit. $^{32}$P-dCTP was incorporated into the reaction to monitor the progress of cDNA synthesis as well as to allow for analysis by alkaline agarose gel electrophoresis. The results of the reverse transcription indicated that the JHK-viral RNA could be primed for RT with oligo-dT, suggesting that the RNA is polyadenylated. Incorporation of label into the cDNA showed appropriate kinetics for an RT reaction. Analysis of the $^{32}$P-labeled cDNA by alkaline agarose gel electrophoresis showed bands ranging from approximately 7000 bp to less than 200 bp.

The second strand was synthesized with DNA polymerase Klenow fragment, EcoR-1 linkers were added, and the cDNA inserted into a pUC19 plasmid vector to make a cDNA library. The cDNA library was made from cDNA fragments ranging in size from about 200 to 8000 base pairs.

Of the >100 *E. coli* delta m15 transformants, the inserts of 30 clones were sized and six inserts (ranging in size from 200 bp to 3000 bp) were further analyzed.

Four cDNA clones (of approximate sizes 600, 700, 1300 and 3000 bp) of JHK viral RNA hybridized by Northern blotting with the RNA from doubly-sucrose-gradient-purified JHK virus. The sequencing of the 694 bp clone (#23) has been completed and is presented in SEQ ID NO:1.

Such cDNA probes will provide powerful analytic reagents for molecular studies and diagnosis for the presence and nature of JHK viral genes. For example, cDNA probes can be used as (i) Southern hybridization probes for analysis of infected cells, tissues, and blood samples; (ii) in situ hybridization probes, especially as detectable by light and electron microscopy, and (iii) probes for the study of virus replication, e.g., by Northern analysis of viral mRNA transcripts. Once we have developed specific cDNA probes and primers, it will be possible to search for similar sequences by hybridization in the PMCs of patients with CFIDS, lymphoma, leukemia, and neuromuscular diseases.

10. Monoclonal and Polyclonal Antibodies.

We have three antibody detection systems: (1) an electron microscope JHK virion microagglutination technique, with which the sera from Patient 1 and the hyperimmunized rabbit and mice are always positive; (2) Western immunoblotting with purified JHK viral antigen, and (3) an ELISA test with JHK viral antigen (from sucrose-gradient-purified virus) run in parallel with EBV antigen from induced, chronically infected, marmoset B958 cells. In these tests, the sera from Patient 1 are positive for JHK viral antigen, and the serum from ND, the normal donor of the lymphocytes that the JHK virus originally infected to produce the JHK-3 cell line, is negative.

We have immunized Balb/c and Balb/c×DBA hybrid mice with sucrose-gradient-purified 80-nm viral pellets mixed with immunologic adjuvant. After three intraperitoneal injections, all the mice have serum antibodies to sucrose-gradient-purified JHK virus as assayed by ELISA. Sera from five of the six Balb/c mice that we have immunized with sucrose-gradient-purified JHK virus contained antibodies that agglutinate JHK virus as visualized by electron microscopy: one mouse at a 1:100 serum dilution, another at a 1:50 dilution, and three at 1:20 dilution. Neither pre-immune mouse serum, normal rabbit serum, nor serum from a healthy human subject agglutinated JHK virions. No spontaneous agglutination of virions has ever been seen in the many ultracentrifuged preparations of JHK virus. To confirm the antibody-related basis for this microagglutination technique, colloidal gold spheres conjugated with goat IgG made against the appropriate, corresponding species immunoglobulin were included to show that the antibodies were present in the aggregates of JKH virions.

Utilizing the electron microscopic microagglutination technique described above, we have shown that serum taken from the Patient 1 in April 1989 and April 1991 agglutinated JHK virions demonstrable at dilutions of 1:20 and 1:50. Serum from a normal human subject N.D. did not agglutinate JHK virus. The demonstration of agglutinating, immunoblotting, and ELISA-reative antibodies to JHK virus in serum of Patient 1 is confirmatory evidence of a link between the virus that we have isolated and this patient.

We envision that polyclonal antibodies can be prepared in rabbits with highly purified 80-nm virus particles, preferably from productively infected lymphoblastoid cell lines such that we can absorb out cell-reactive antibodies with the parent lines. These antibodies should be powerful reagents for Western immunoblotting and further purification of virus, as well as for the determination of possible cross-relatedness with HIV, HTLV, bovine leukemia virus, and selected primate and murine viruses.

Monoclonal antibodies can be prepared by fusing in vitro the splenocytes from the above-referenced immunized mice with plasmacytoma cells by standard methods (e.g., *Antibodies, A Laboratory Manual*, E. Harlow and D. Lane, Cold Spring Harbor Laboratory, 1988) and screening the supernatant fluids of cultures of outgrowths of the fused cells by JHK viral immunoblots and ELISA assays. Antibodies from the supernatants of cultures positive for JHK virus and negative for EBV can be purified by standard methods (e.g., Harlow and Lane, supra).

11. Assay to Detect the Presence or Absence of JHK Virus Infection. Antibodies specific for JHK virion antigens, nucleic acid probes specific for JHK sequences and viral antigens specific for JHK antibodies all provide means for detecting the presence or absence of JHK virus infection.

a. Antibody-dependent assays

Western Blotting. One method to determine whether a patient has been infected with the JHK virus is a Western immunoblotting analysis.

We performed a Western blot as follows: preparations of JHK virus that had been purified by banding twice in sequence in sucrose gradients were used as the source of antigen. The virus was disrupted by boiling in gel-loading Laemmli buffer, and the viral proteins were electrophoresed on SDS-polyacrylamide gels. The proteins were electrophorectically transferred to nitrocellulose, and strips of this paper with the immobilized viral proteins were reacted with sera from patients or immunized animals. After incubation with test sera, the strips were washed and reacted with $^{125}$I-labeled protein A to detect antigen-antibody complexes, and the radioactivity was detected by autoradiography.

Figure 5:
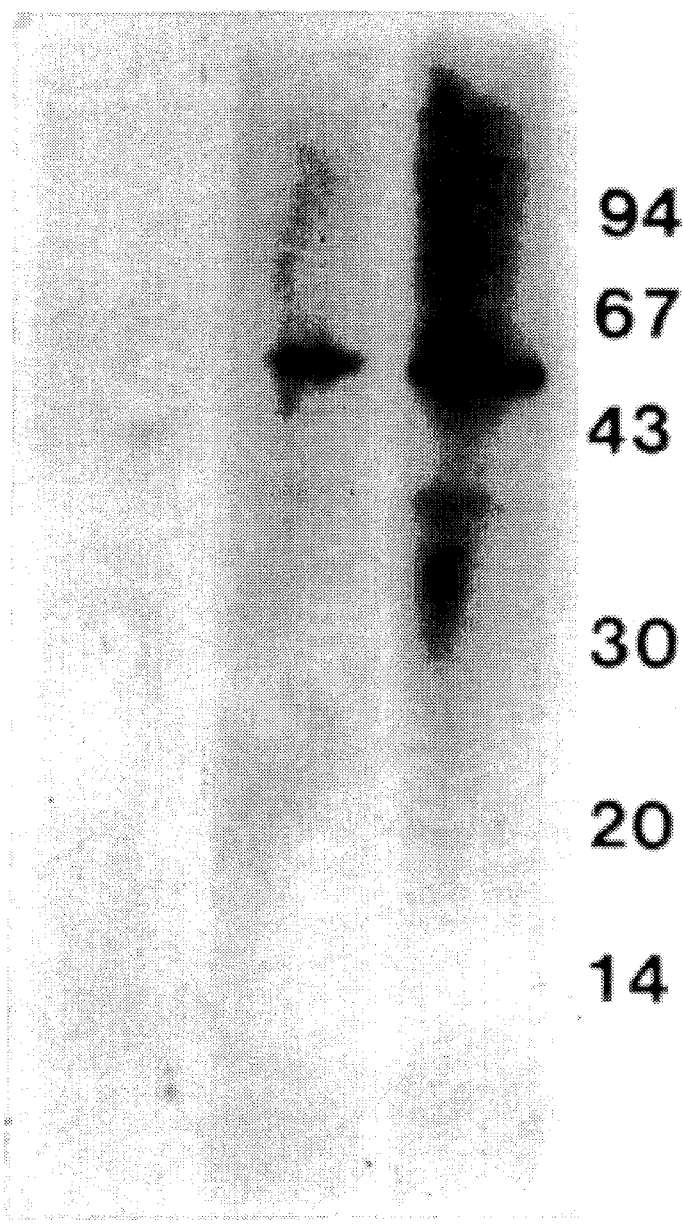
FIG. 5 is the result of a Western immunoblot experiment in which serum samples from Patient 1 and a normal donor are exposed to electrophoresed JHK viral proteins.

FIG. 5 is an example of a Western blot. FIG. 5 shows the results of reacting the electrophorased JHK viral proteins with a 1:200 dilution of sera from the normal donor ND and from Patient 1, from whom blood samples were taken in April 1989, designated as P1-1, and in April 1991, designated P1-2. Note the relatively prominent bands of approximate molecular weights 38,000 and 58,000 that react with the patient's sera and not with the serum of the normal donor.

ELISA. Another tool to analyze a patient's serum for the presence of an antibody against a JHK antigen is an ELISA (enzyme-linked immunosorbent assay). In general, a purified viral-specific antigen (either the virus or a viral protein) is coated onto an assay plate. The patient's serum is allowed to contact the coated plates. Various methods are used to assay for the presence of the antigen-antibody complex.

More specifically, an ELISA may be run in the following manner: JHK viral antigen (100 ng/100 μl/well) is absorbed overnight at 4° C. onto Dynatech immulon plastic plates in coating buffer (0.025 M NaHCO$_3$ and Na$_2$CO$_3$, pH 9.6, NaN$_3$ 0.02%). The plates are washed 5 times with PBS-Tween. The serum sample (primary antibody) is serially diluted in phosphate-buffered saline (PBS)-0.0005% Tween-20, containing 100 μg/ml fetal bovine serum (FBS) as blocking protein to reduce background (non-specific absorption). 100 μl of each dilution is added to wells in duplicate, and the plates are incubated overnight at 4° C. (or 2 hours at 20° C. with rocking). The plates are then washed 5 times with PBS-Tween, and 100 μl goat anti-Human IgG Fab (secondary antibody) conjugated with alkaline phosphatase diluted in PBS-Tween containing 100 μg/ml FBS is added.

The plates are washed 5 times with PBS-Tween, and paranitrophenylphosphate substrate 1 mg/ml in diethanolamine buffer (50 µl/well) is added for 10 minutes at 20° C. The reaction is stopped with 50 µl/well 1.0N NaOH, and the absorbance measured at 405 nm versus the blank containing no antigen or antibody. Appropriate controls consist of antigen alone, primary antibody plus antigen, and secondary antibody plus antigen alone. To calculate the titer of the serum antibody, a dose-response curve is constructed by plotting the absorbance against the serum dilutions, and where the line intercepts the endpoint (i.e., the value three times the standard deviation above the negative controls) is taken as the titer, i.e., the dilution of serum at the endpoint.

Any type of in vitro immunological test can be used to detect JHK viral antibodies with a purified viral preparation or viral extract: direct or indirect immunofluorescence, biotinylated antibodies or immunoenzymatic assays, or radioimmunoprecipitation tests can be employed.

The invention also relates to virus preparations labeled by radioactive or nonradioactive techniques, e.g., enzymatic, flourescent, biotinylated antibody or by any other nonradioactive means.

b. Assays to detect JHK viral antigens. Other methods involve examining the patient's tissues, cells or fluids for JHK antigen. Possible methods include utilizing specific polyclonal antibodies raised in animals, or monoclonal antibodies, or antibodies from Patient 1. Suitable tests include ELISA assays as described above, radioimmune assays, radioimmunoprecipitation or biotinylation assays of the direct or indirect type. Immunoelectron microscopy utilizing antibodies labelled with electron-dense substances, e.g., colloidal gold or agglutination by antibody of viral particles observable by electron microscopy can also be used.

For immunoelectron microscopy to detect the viral particles associated with B-lymphocytes in a patient's peripheral blood, indirect methods that utilize protein-A or protein-G or anti-human IgG labeled with colloidal gold should not be utilized because B-lymphocytes normally produce IgG, IgM, and possess Fc receptors. Therefore, anti-JHK viral antibodies as described above, or from Patient 1, are chromatographed through a Protein-G column to purify the IgG. The IgG is then absorbed with sucrose gradient-purified Epstein-Barr virus (EBV) prepared in marmoset B958 cells to bind anti-EBV antibodies and the antigen-antibody complexes then removed. The residual uncomplexed IgG is treated with pepsin to obtain F(ab')$_2$ fragments which are then conjugated with colloidal gold. B-lymphocytes or cultured cells, in which one wishes to detect JHK viral antigens, are incubated with the F(ab')$_2$ fragments conjugated with colloidal gold prior to fixation, embedded in Epon, and thin-sectioned for observation by electron microscopy to determine specific binding of labelled antibody to viral antigens. Scanning electron microscopy may be used as alternative technique of observing whole (not sectioned) labelled cells. (D. J. Brigati, et al., *Virology*, 126:32–50, 1986; N. J. Hutchinson, et al., *J. Cell Biol.*, 95:609–618, 1982).

c. Nucleic Acid Hybridization.

With nucleic acid probes specific to JHK virus, one may determine whether these sequences are present in the host DNA, thus indicating that the JHK virus is in the proviral state, or for the detection of viral RNA transcripts. Possible methods include: Southern analyses or dot-blot hybridization can utilize different amounts of DNA extracted from the patient's tissue or cells or polymerase chain reaction standard techniques can be used to amplify cellular DNA or RNA, for example, from white blood cells, (see E. DeFreitas et al. *Proc. Natl. Acad. Sci. USA*, 88:2922–6, 1991). Northern analyses can be done with $^{32}$P-labelled cDNA or biotinylated probes and can be performed with RNA extracted from patient's cells or in fixed cells by in situ hybridization via standard light microscopy techniques (A. T. Haase, *J. Histochem. Cytochem.*, 34:27–32, 1986) or by EM methods (M. Binder, et al., *J. Cell Biol.*, 102:1646–1653, 1986). The polymerase chain reaction can be utilized with nucleic acid primers, constructed from the genomic clones of the JHK virus, to detect the presence of JHK viral DNA in patients' tissue, white blood cells or fluids by standard amplification techniques (*PCR Protocols: A Guide to Methods and Applications*, M. A. Innes, et al., eds., Academic Press, San Diego, 1992, 482 pages; *Molecular Cloning: A Laboratory Manual*, J. Sambrook, et al., 2nd edition, Cold Spring Harbor Laboratory Press, 1989, vol. 2).

---

We claim:

1. The isolated cell line ATCC No. CRL10991 which produces an NMA virus wherein the NMA virus is between 80 nanometers and 85 nanometers in size.

2. An isolated NMA virus produced by the cell line ATCC No. CRL10991, wherein the NMA virion is between 80 nanometers and 85 nanometers in size.

* * * * *